(12) United States Patent
Lee

(10) Patent No.: US 11,383,018 B2
(45) Date of Patent: Jul. 12, 2022

(54) SURGICAL INSTRUMENT FOR SUCTION AND IRRIGATION

(71) Applicant: ORANGE MEDICS, INC., Daejeon (KR)

(72) Inventor: Ki Hwan Lee, Daejeon (KR)

(73) Assignee: ORANGE MEDICS, INC., Daejeon (KR)

( * ) Notice: Subject to any disclaimer, the term of this patent is extended or adjusted under 35 U.S.C. 154(b) by 242 days.

(21) Appl. No.: 16/643,598

(22) PCT Filed: Oct. 12, 2018

(86) PCT No.: PCT/KR2018/012010
§ 371 (c)(1),
(2) Date: Mar. 2, 2020

(87) PCT Pub. No.: WO2019/078546
PCT Pub. Date: Apr. 25, 2019

(65) Prior Publication Data
US 2021/0402076 A1     Dec. 30, 2021

(30) Foreign Application Priority Data
Oct. 17, 2017 (KR) .................. 10-2017-0134352

(51) Int. Cl.
*A61M 1/00* (2006.01)
*A61B 17/00* (2006.01)
*A61M 3/02* (2006.01)

(52) U.S. Cl.
CPC ....... *A61M 1/774* (2021.05); *A61B 17/00234* (2013.01); *A61M 1/7413* (2021.05);
(Continued)

(58) Field of Classification Search
CPC .... A61M 1/774; A61M 1/7413; A61M 1/772; A61M 1/741; A61M 1/743; A61M 1/76;
(Continued)

(56) References Cited

U.S. PATENT DOCUMENTS 10,448,814 B2 * 10/2019 Rebholz ................. A61B 1/015
2002/0082475 A1    6/2002 Stahl et al.
(Continued)

FOREIGN PATENT DOCUMENTS

EP            537573 A2    4/1993
KR        10-0389006 B1    6/2003
(Continued)

OTHER PUBLICATIONS

International Search Report for PCT/KR2018/012010 dated Jan. 11, 2018 from Korean Intellectual Property Office.

*Primary Examiner* — Bhisma Mehta
*Assistant Examiner* — Phoebe Anne Staton
(74) *Attorney, Agent, or Firm* — Revolution IP, PLLC

(57) ABSTRACT

A surgical instrument for suction and irrigation, includes: an insertion tube inserted into the body of a patient; an instrument body coupled to the insertion tube and disposed outside the body of the patient; an irrigation fluid control valve coupled to the instrument body; and a drainage fluid control valve coupled to the instrument body and separated a predetermined distance from the irrigation fluid control valve in a longitudinal direction of the instrument body.

11 Claims, 9 Drawing Sheets

(52) U.S. Cl.
CPC .......... *A61M 1/772* (2021.05); *A61M 3/0279* (2013.01); *A61B 2217/005* (2013.01); *A61B 2217/007* (2013.01)

(58) Field of Classification Search
CPC ...... A61M 1/77; A61M 39/22; A61M 3/0283; A61M 2039/224; A61M 1/0062; A61M 1/0058; A61B 17/00234; A61B 1/015; A61B 2217/005; A61B 2217/007; A61C 17/0202; A61C 17/0217
See application file for complete search history.

(56) References Cited

U.S. PATENT DOCUMENTS

| | | | |
|---|---|---|---|
| 2011/0230823 A1* | 9/2011 | Simonsen | A61M 1/774 604/30 |
| 2015/0094709 A1* | 4/2015 | Elliott | A61B 18/14 606/34 |
| 2017/0100526 A1* | 4/2017 | Teng | A61M 39/22 |

FOREIGN PATENT DOCUMENTS

| | | |
|---|---|---|
| KR | 10-2015-0061897 A | 6/2015 |
| WO | 2004-075715 A2 | 9/2004 |

\* cited by examiner

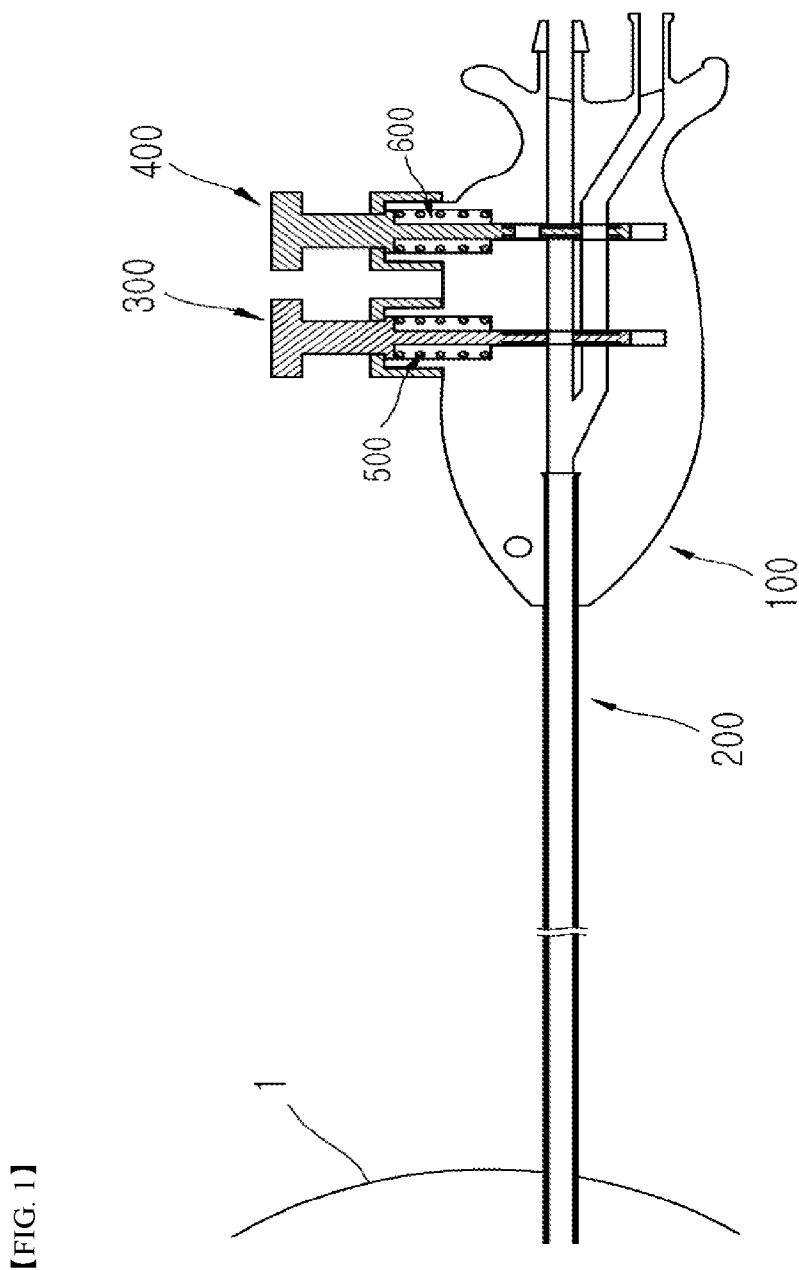
[FIG. 1]

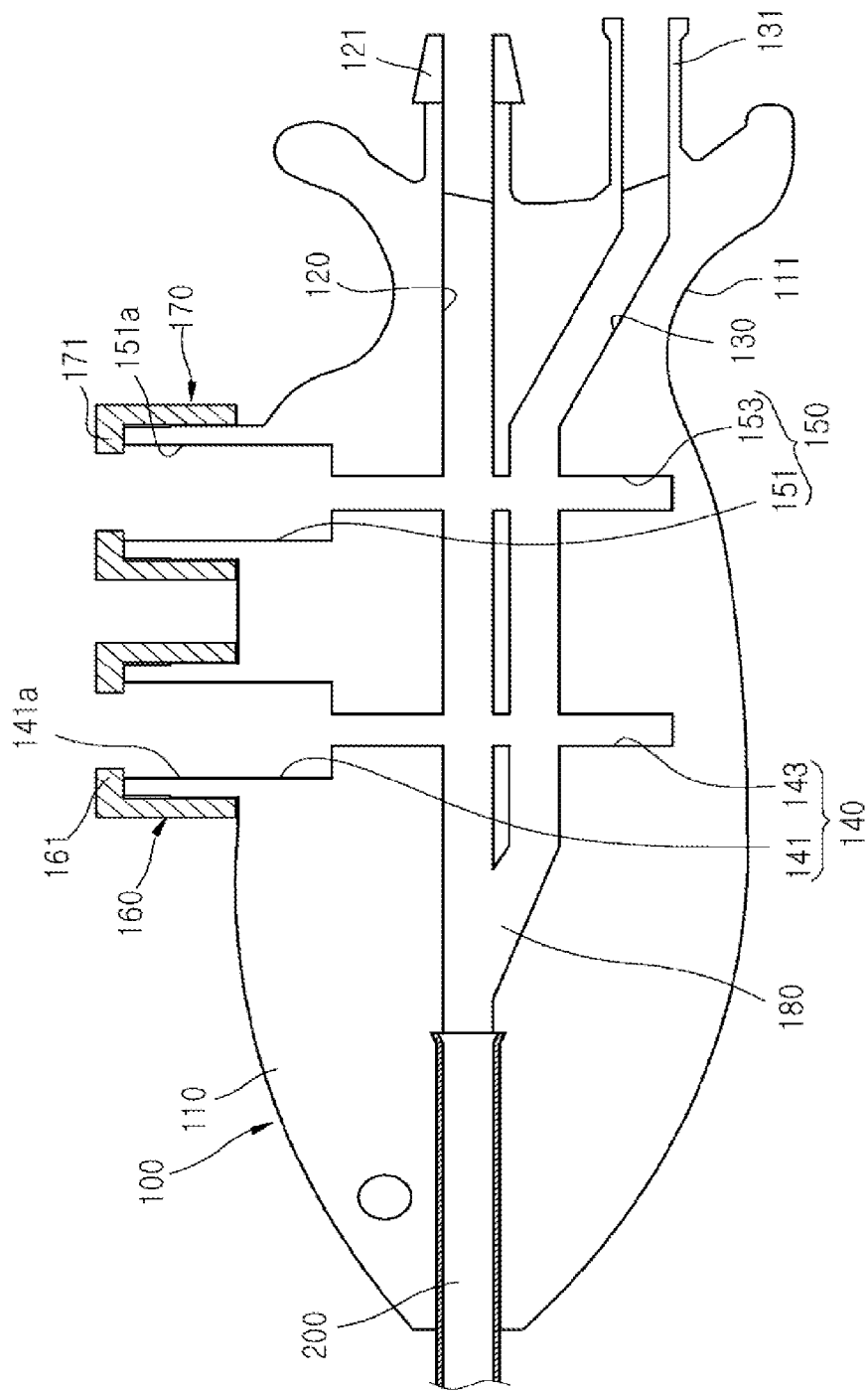
[FIG. 2]

[FIG. 3]
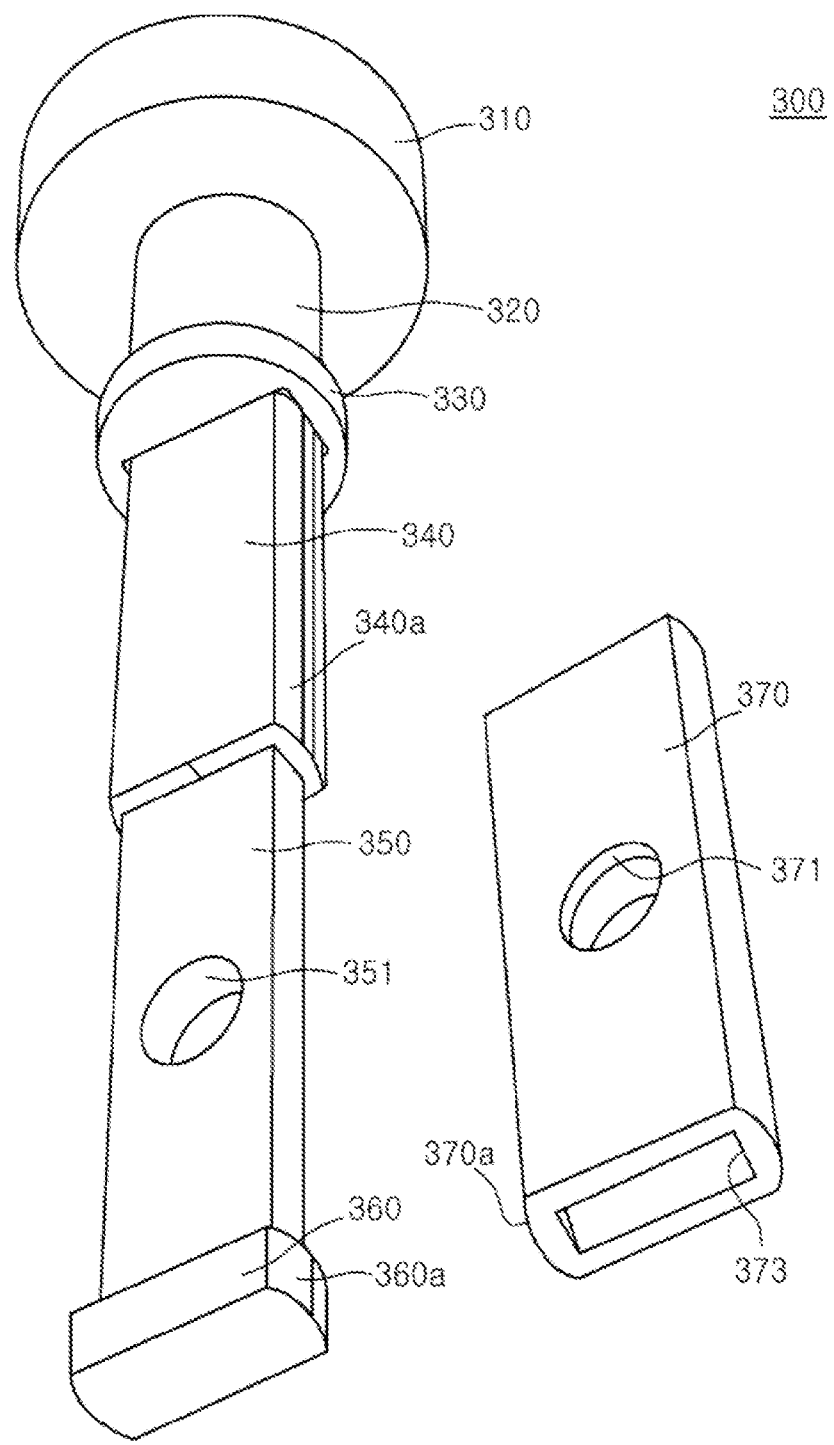

[FIG. 4]
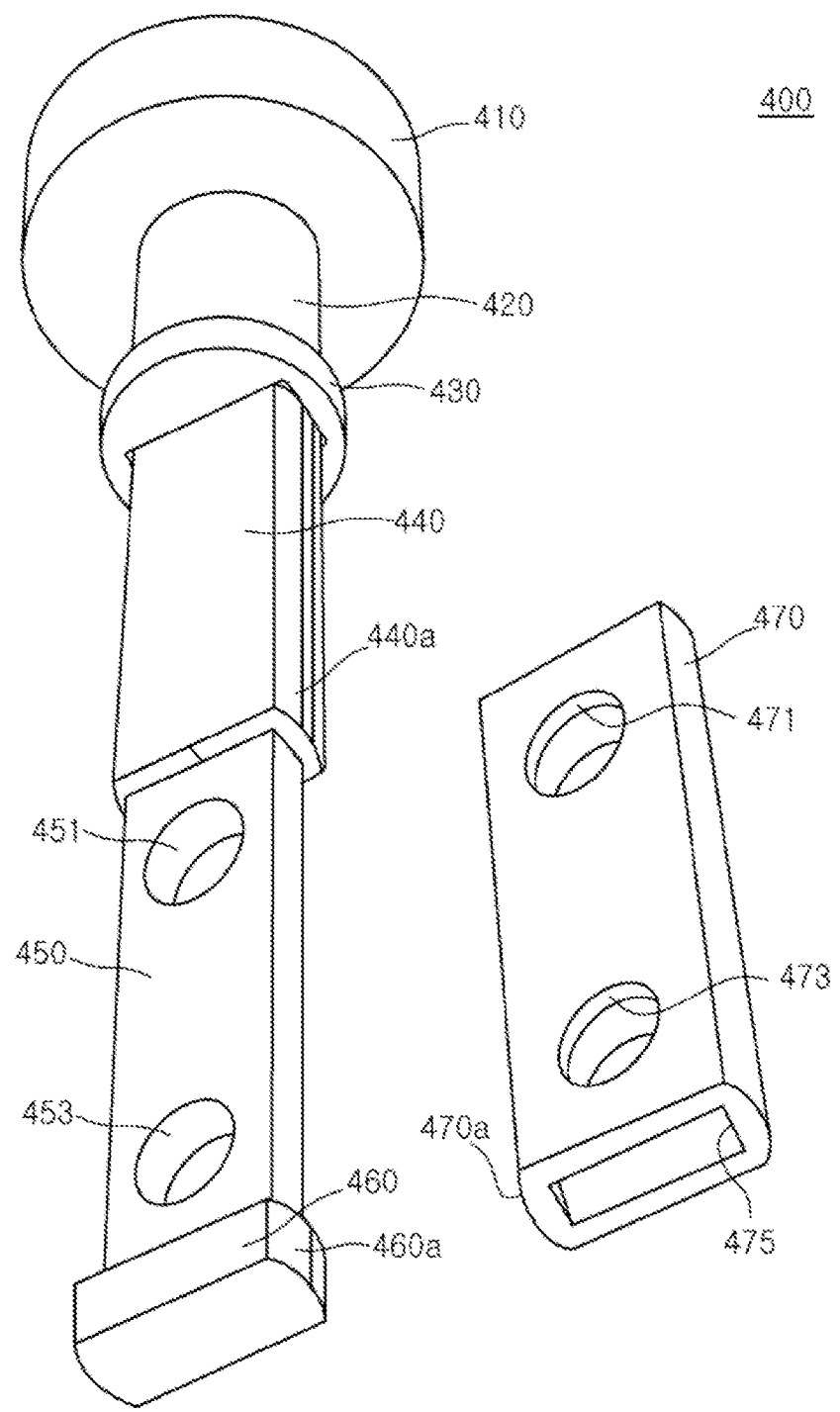

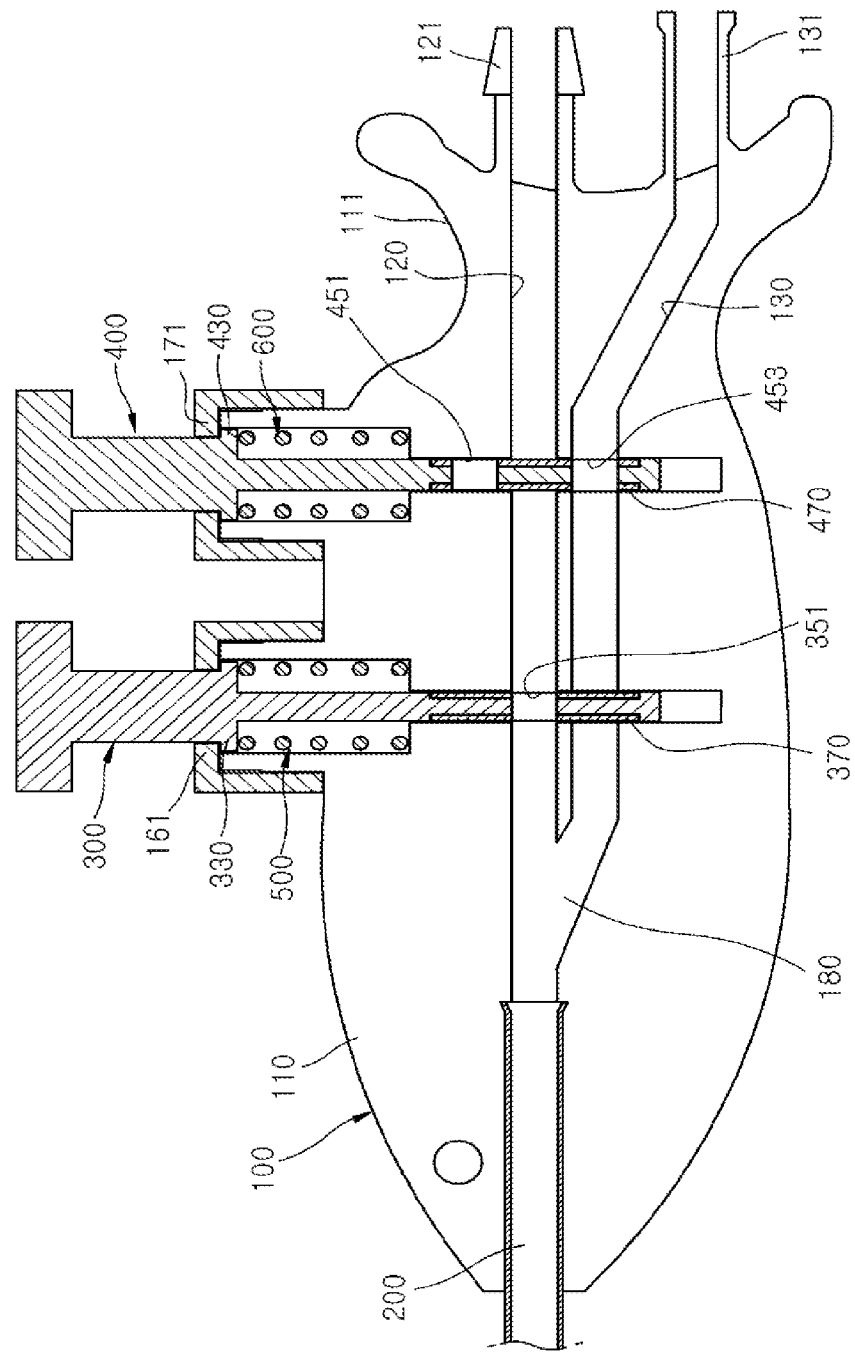
[FIG. 5]

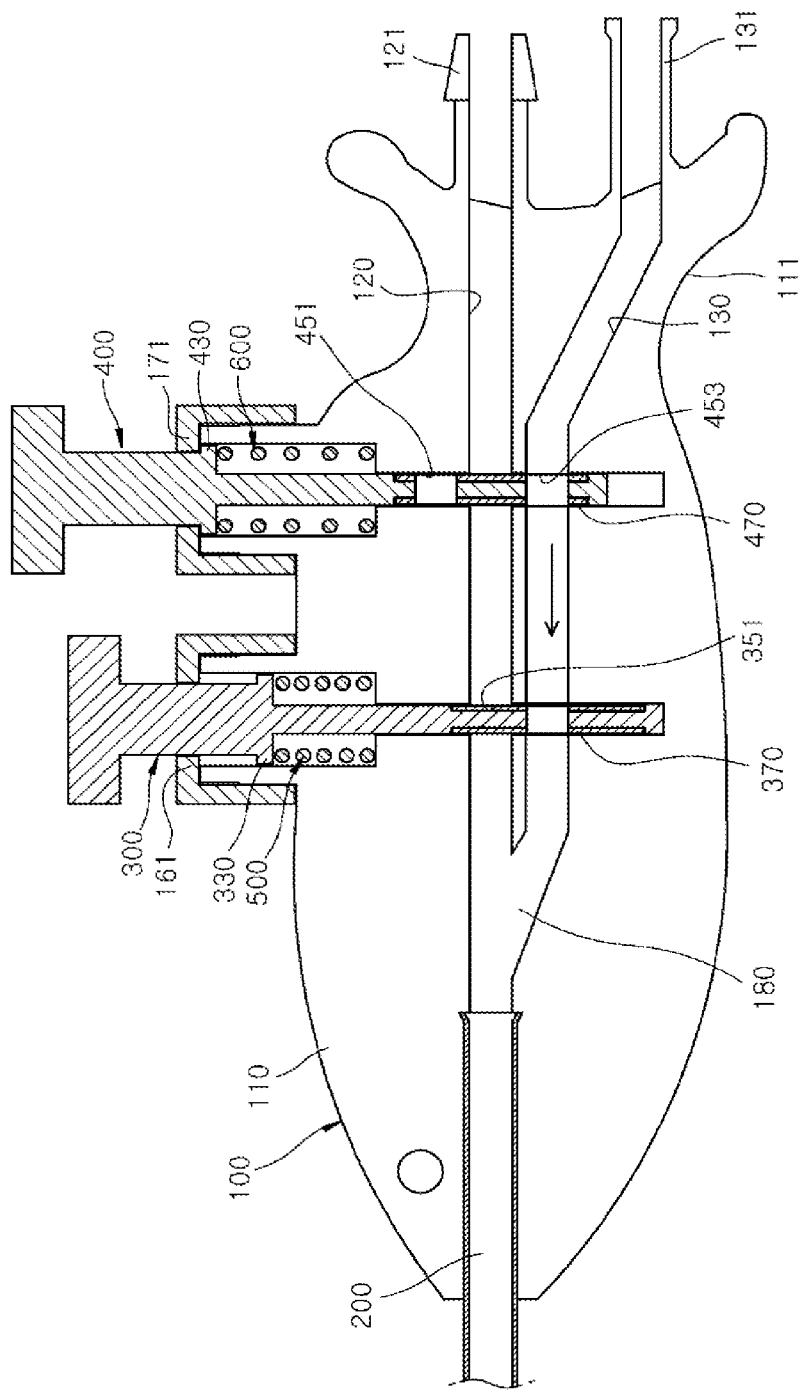
[FIG. 6]

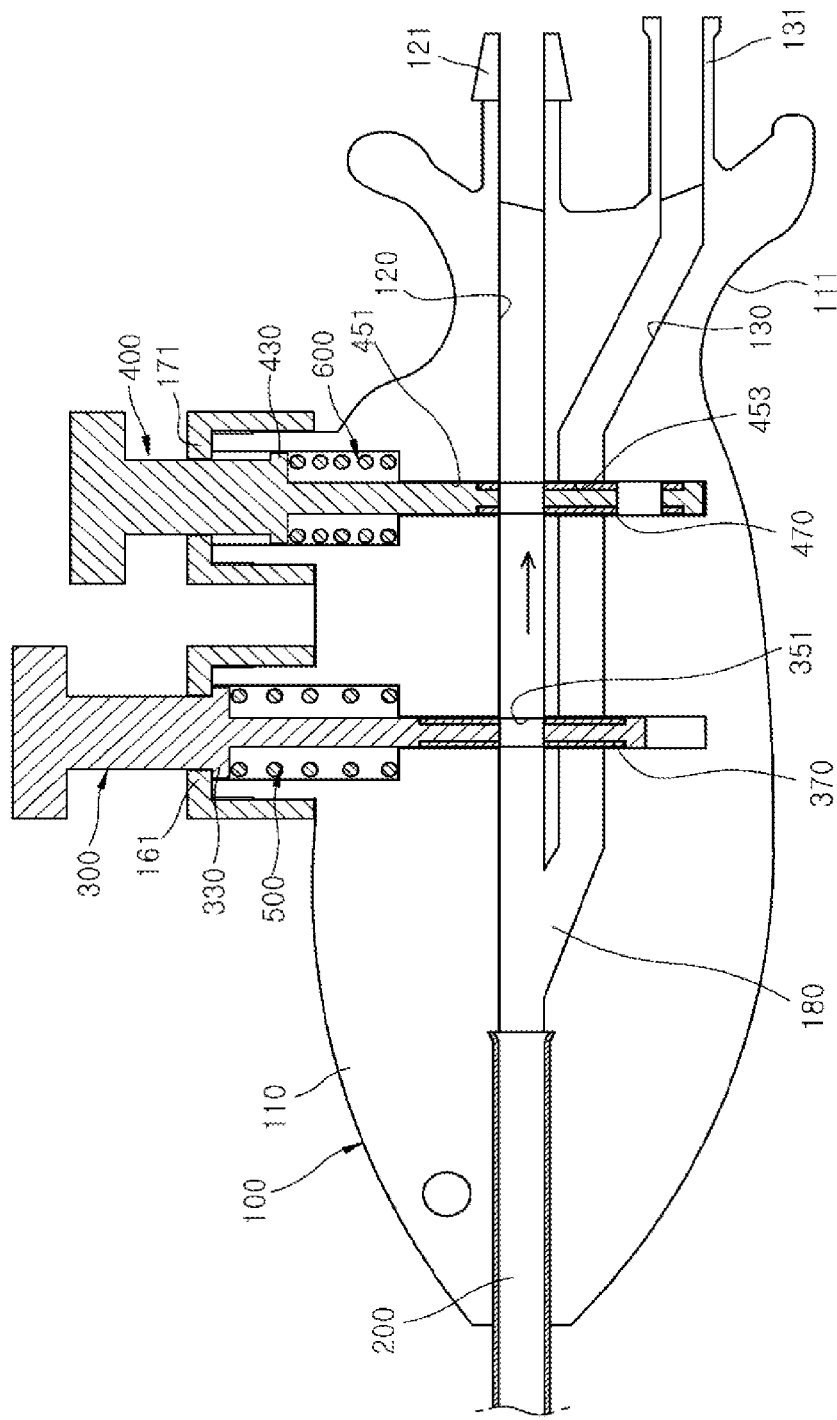
[FIG. 7]

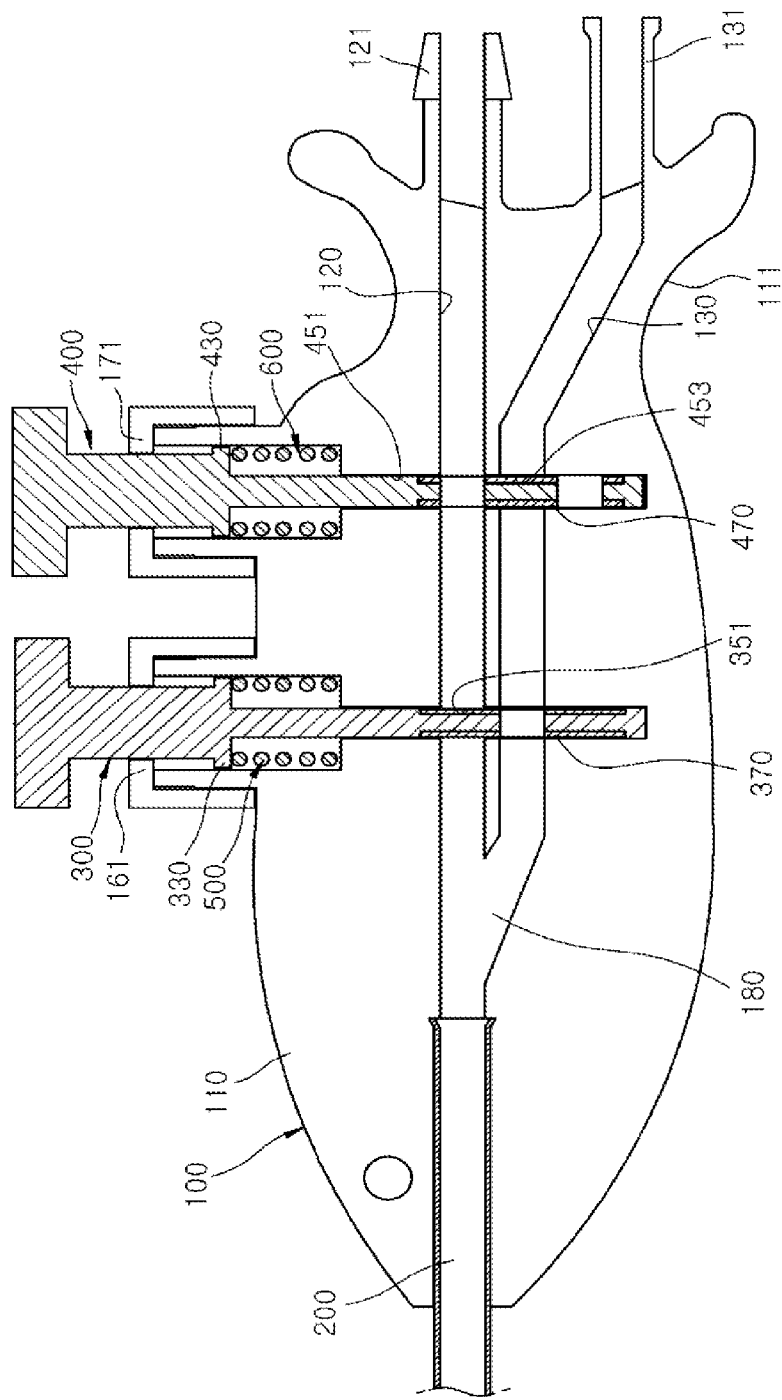
[FIG. 8]

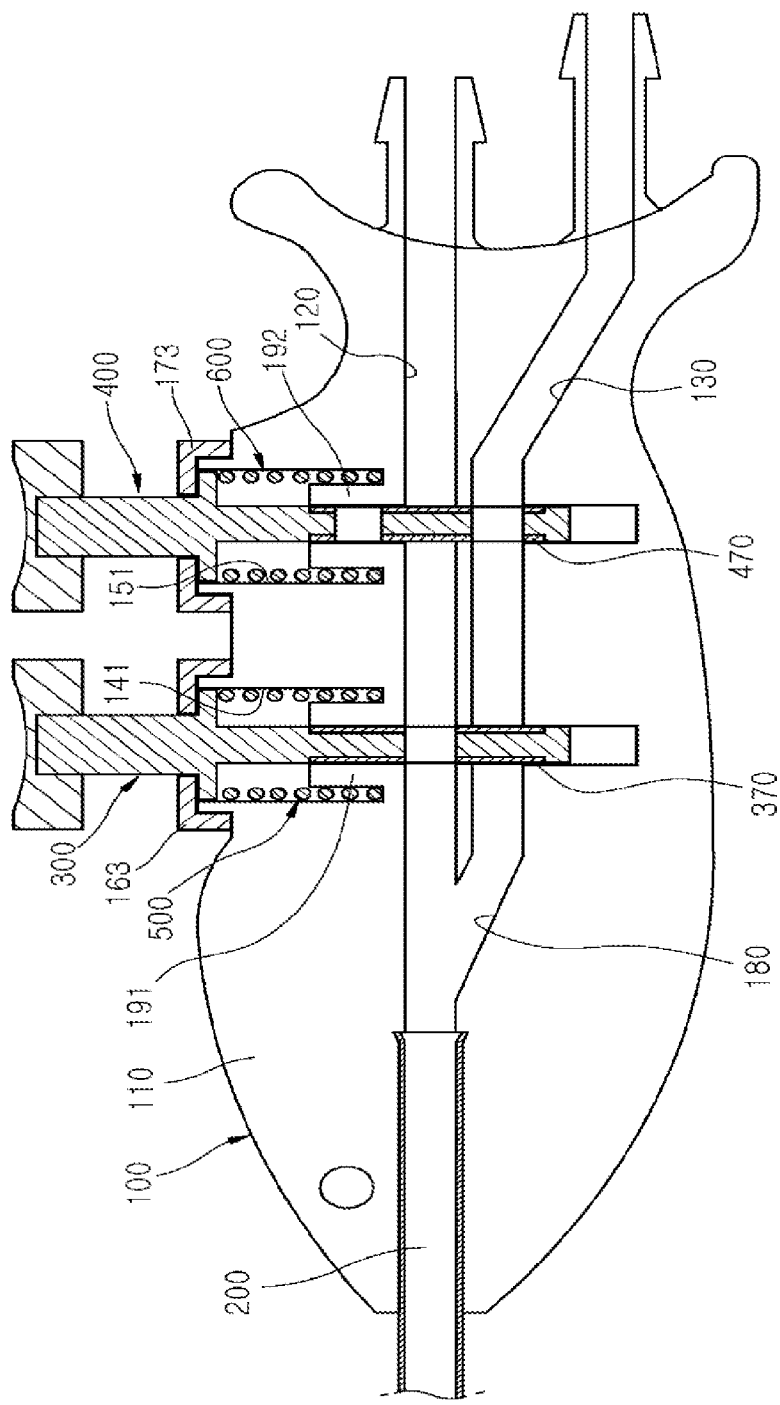
[FIG. 9]

SURGICAL INSTRUMENT FOR SUCTION AND IRRIGATION

TECHNICAL FIELD

The present invention relates to a surgical instrument, and more particularly, to a surgical instrument for suction and irrigation which allows, during a surgical operation, simple and efficient control over opening/closing of an irrigation fluid inlet channel adapted to supply an irrigation fluid into the body of a patient therethrough and a contaminated fluid outlet channel adapted to discharge a contaminated fluid therethrough after irrigation of an inside of the body of the patient.

BACKGROUND ART

In general, endoscopic (or laparoscopic) surgery is minimally invasive surgery and is booming recently due to advantages of reducing pain, infection, wounds, hospitalization, and the like of a patient.

In laparoscopic surgery, a surgical instrument which supplies an irrigation fluid for irrigation of a surgical site of a patient and discharges a contaminated fluid from the body of the patient after irrigation of the surgical site of the patient, that is, a laparoscopic suction and irrigation system, is used.

A typical laparoscopic suction and irrigation system includes an insertion tube inserted into the body of a patient, an instrument body having a mixing chamber connected to the insertion tube, an irrigation channel connected to the mixing chamber to supply an irrigation fluid into the body of the patient, and an outlet channel connected to the mixing chamber separately from the irrigation channel to discharge a contaminated fluid from the body of the patient.

In addition, the laparoscopic suction and irrigation system further includes an irrigation channel control valve disposed only on the irrigation channel and an outlet channel control valve disposed only on the outlet channel.

Here, since the insertion tube, the mixing chamber, the irrigation channel, and the outlet channel are not placed in the same plane, the irrigation channel and the outlet channel are bent from the instrument body.

Thus, such a typical laparoscopic suction and irrigation system has a problem of increase in manufacturing costs due to components required for these bent channels. In particular, the bent outlet channel causes reduction in suction force of the system.

One example of the related art is disclosed in Korean Patent Registration No. 1546488 (titled "Suction and Irrigator", registration published on Aug. 21, 2015).

DISCLOSURE

Technical Problem

It is one aspect of the present invention to provide a surgical instrument for suction and irrigation which allows, during a surgical operation, simple and efficient control over opening/closing of an irrigation fluid inlet channel adapted to supply an irrigation fluid into the body of a patient therethrough and a contaminated fluid outlet channel adapted to discharge a contaminated fluid therethrough after irrigation of an inside of the body of the patient.

It is another aspect of the present invention to provide a surgical instrument for suction and irrigation which allows reduction in the number of required components, thereby reducing manufacturing costs.

Technical Solution

In accordance with one aspect of the present invention, a surgical instrument for suction and irrigation includes: an insertion tube inserted into the body of a patient; an instrument body coupled to the insertion tube and disposed outside the body of the patient; an irrigation fluid control valve coupled to the instrument body; and a drainage fluid control valve coupled to the instrument body and separated a predetermined distance from the irrigation fluid control valve in a longitudinal direction of the instrument body.

The instrument body may include a main body, wherein the main body is formed with a connection channel communicating with the insertion tube, an irrigation fluid inlet channel branched off of the connection channel and adapted to supply an irrigation fluid into the body of the patient therethrough, and a contaminated fluid outlet channel branched off of the connection channel and adapted to suction a contaminated fluid therethrough after irrigation of an inside of the body of the patient.

Each of the irrigation fluid control valve and the drainage fluid control valve may be disposed in the instrument body to pass through both the irrigation fluid inlet channel and the contaminated fluid outlet channel and may be moved by external force to selectively open/close the irrigation fluid inlet channel and the contaminated fluid outlet channel.

Specifically, when no external force is applied, the irrigation fluid control valve opens the contaminated fluid outlet channel while closing the irrigation fluid inlet channel and the drainage fluid control valve opens the irrigation fluid inlet channel while closing the contaminated fluid outlet channel.

When the irrigation fluid control valve is moved in a first direction corresponding to a direction of an inner space of the main body by external force with no external force applied to the drainage fluid control valve, the irrigation fluid control valve closes the contaminated fluid outlet channel while opening the irrigation fluid inlet channel such that the irrigation fluid can be supplied into the body of the patient along the irrigation fluid inlet channel.

When the drainage fluid control valve is moved in the first direction corresponding to the direction of the inner space of the main body by external force with no external force applied to the irrigation fluid control valve, the drainage fluid control valve closes the irrigation fluid inlet channel while opening the contaminated fluid outlet channel such that the contaminated fluid can be suctioned out of the body of the patient along the contaminated fluid outlet channel.

The surgical instrument may further include: a first elastic member disposed in the main body to provide elastic restoring force against movement of the irrigation fluid control valve; and a second elastic member disposed in the main body to provide elastic restoring force against movement of the drainage fluid control valve.

The main body may be formed with a first installation space into which the irrigation fluid control valve is partially inserted and a second installation space into which the drainage fluid control valve is partially inserted.

The first installation space may include a first upper installation space and a first lower installation space downwardly extending from the first upper installation space and having a smaller cross-sectional width than the first upper installation space.

The instrument body may further include a first retention cap coupled to the main body to prevent the irrigation fluid control valve from being separated from the main body. Here, the first retention cap may be coupled to an upper edge of the first upper installation space.

The irrigation fluid control valve may include: a first valve head exposed outside the main body; a first extension downwardly extending from the first valve head; a first locking portion downwardly extending from the first extension and having a larger diameter than the first extension; and a first leg downwardly extending from the first locking portion.

The first leg may include a first upper leg downwardly extending from the first locking portion and a first lower leg downwardly extending from the first upper leg and having a smaller cross-sectional width than the first upper leg.

The first lower leg may be formed with a first communication hole selectively communicating with the irrigation fluid inlet channel and the contaminated fluid outlet channel.

The irrigation fluid control valve may further include a first sealing portion disposed on at least a portion of an outer surface of the first lower leg to seal off the first installation space from the irrigation fluid inlet channel and the contaminated fluid outlet channel.

The first sealing portion may be formed with a first sealing hole communicating with the first communication hole.

A side surface of the first upper leg and a side surface of the first sealing portion may be rounded to allow the irrigation fluid control valve to be smoothly moved in the first installation space.

The drainage fluid control valve may be formed with a second communication hole selectively communicating with the contaminated fluid outlet channel and a third communication hole selectively communicating with the irrigation fluid inlet channel.

A central cross-section of the connection channel, a central cross-section of the irrigation fluid inlet channel, and a central cross-section of the contaminated fluid outlet channel may be placed in the same plane in the longitudinal direction of the instrument body.

Advantageous Effects

The surgical instrument for suction and irrigation according to the present invention has the following effects:

First, since the irrigation fluid inlet channel, the contaminated fluid outlet channel, the irrigation fluid control valve, and the drainage fluid control valve are placed in the same plane in the longitudinal direction of the instrument body and the irrigation fluid control valve and the drainage fluid control valve are moved by external force to selectively open/close the irrigation fluid inlet channel and the contaminated fluid outlet channel, supply of the irrigation fluid and suction of the contaminated fluid can be efficiently achieved with a simple structure.

Second, since a structure for selectively opening/closing the irrigation fluid inlet channel and the contaminated fluid outlet channel is simplified, the number of required components can be reduced, thereby allowing reduction in manufacturing costs.

DESCRIPTION OF DRAWINGS

FIG. 1 is a sectional view of a surgical instrument for suction and irrigation according to one embodiment of the present invention, wherein the surgical instrument is in use.

FIG. 2 is a view of an instrument body of the surgical instrument of FIG. 1.

FIG. 3 is a view of an irrigation fluid control valve of the surgical instrument of FIG. 1.

FIG. 4 is a view of a drainage fluid control valve of the surgical instrument of FIG. 1.

FIG. 5 is a view of the irrigation fluid control valve and the drainage fluid control valve of the surgical instrument of FIG. 1, with no external force applied thereto.

FIG. 6 is a view of the irrigation fluid control valve and the drainage fluid control valve of the surgical instrument of FIG. 1, with external force applied only to the irrigation fluid control valve.

FIG. 7 is a view of the irrigation fluid control valve and the drainage fluid control valve of the surgical instrument of FIG. 1, with external force applied only to the drainage fluid control valve.

FIG. 8 is a view of the irrigation fluid control valve and the drainage fluid control valve of the surgical instrument of FIG. 1, with external force applied to both the irrigation fluid control valve and the drainage fluid control valve.

FIG. 9 is a view of a surgical instrument according to another embodiment of the present invention.

BEST MODE

Hereinafter, embodiments of the present invention will be described with reference to the accompanying drawings. It should be noted that like components will be denoted by like reference numerals and like names and repeated description thereof will be omitted.

FIG. 1 is a cross-sectional view of a surgical instrument for suction and irrigation according to one embodiment of the present invention, wherein the surgical instrument is in use, and FIG. 2 is a view of an instrument body of the surgical instrument of FIG. 1.

Referring to FIG. 1 and FIG. 2, the surgical instrument includes an insertion tube 200, an instrument body 100, an irrigation fluid control valve 300, a drainage fluid control valve 400, a first elastic member 500, and a second elastic member 600.

The insertion tube 200 is insertable at one end thereof into the body of a patient 1 and is coupled at the other end thereof to the instrument body 100.

The instrument body 100 is coupled to the insertion tube 200, is placed outside the body of the patient 1, and has a generally fish-like shape.

The instrument body 100 is formed with a coupling portion (not shown) allowing the other end of the insertion tube 200 to be inserted thereinto and coupled thereto. Here, the other end of the insertion tube 200 and the coupling portion may be screw-fastened to each other.

The instrument body 100 includes a main body 110, a first retention cap 160, and a second retention cap 170, wherein the first and second retention caps are screw-fastened to the main body 110.

The main body 110 is formed with a connection channel 180 communicating with the insertion tube 200, an irrigation fluid inlet channel 130 branched off of the connection channel 180 and adapted to supply an irrigation fluid into the body of the patient therethrough, and a contaminated fluid outlet channel 120 branched off of the connection channel 180 and adapted to suction a contaminated fluid from the body of the patient therethrough after irrigation of an inside of the body of the patient.

Although not shown in the drawings, an end 131 of the irrigation fluid inlet channel is connected to an external irrigation fluid supply device, and an end 121 of the contaminated fluid outlet channel is connected to an external suction device.

During a surgical procedure, a process of supplying the irrigation fluid along the irrigation fluid inlet channel 130 and a process of discharging the contaminated fluid along the contaminated fluid outlet channel 120 may be repeatedly performed.

Here, the connection channel 180 corresponds to a region where the contaminated fluid outlet channel 120 and the irrigation fluid inlet channel 130 meet each other at angles. In addition, the connection channel 180 is placed in the same plane as the contaminated fluid outlet channel 120 to be in a line with the contaminated fluid outlet channel 120, whereby the amount of the contaminated fluid remaining in the connection channel 180 can be reduced.

As a result, in the process of supplying a new irrigation fluid through the irrigation fluid inlet channel 130, the new irrigation fluid is less likely to be mixed with the contaminated fluid remaining in the connection channel 180 after completion of a preceding discharge process.

In addition, the main body 110 is formed with a first installation space 140 into which the irrigation fluid control valve 300 is partially inserted and a second installation space 150 into which the drainage fluid control valve 400 is partially inserted.

The first installation space 140 includes a first upper installation space 141 and a first lower installation space 143 downwardly extending from the first upper installation space 141 and having a smaller cross-sectional width than the first upper installation space 141.

Similarly, the second installation space 150 includes a second upper installation space 151 and a second lower installation space 153 downwardly extending from the second upper installation space 151 and having a smaller cross-sectional width than the second upper installation space 151.

In addition, the main body 110 is formed with a recessed grip 111 by which a user grasps the instrument body 100.

The first retention cap 160 is coupled to the main body 110 to prevent the irrigation fluid control valve 300 from being separated from the main body 110. Here, the first retention cap 160 may be screw-fastened to an upper edge 141*a* of the first upper installation space which protrudes a predetermined height from the main body 110.

Similarly, the second retention cap 170 is coupled to the main body 110 to prevent the drainage fluid control valve 400 from being separated from the main body 110. Here, the second retention cap 170 may be screw-fastened to an upper edge 151*a* of the second upper installation space which protrudes a predetermined height from the main body 110.

Here, each of the irrigation fluid control valve 300 and the drainage fluid control valve 400 is disposed in the instrument body 100 to pass through both the irrigation fluid inlet channel 130 and the contaminated fluid outlet channel 120. Here, the irrigation fluid inlet channel 130 and the contaminated fluid outlet channel 120 are placed in the same plane.

More specifically, a central cross-section of the insertion tube 200, a central cross-section of the connection channel 180, a central cross-section of the irrigation fluid inlet channel 130, a central cross-section of the contaminated fluid outlet channel 120, a central cross-section of the irrigation fluid control valve 300, and a central cross-section of the drainage fluid control valve 400 may be placed in the same plane in a longitudinal direction of the instrument body 100.

In addition, each of the irrigation fluid control valve 300 and the drainage fluid control valve 400 is moved by external force to selectively open/close the irrigation fluid inlet channel 130 and the contaminated fluid outlet channel 120.

Since the insertion tube 200, the connection channel 180, the irrigation fluid inlet channel 130, and the contaminated fluid outlet channel 120 are placed in the same plane in the longitudinal direction of the instrument body 100, lengths of the connection channel 180, the irrigation fluid inlet channel 130, and the contaminated fluid outlet channel 120 can be shortened, thereby reducing pressure loss during flow of a fluid through the channels.

In particular, since the insertion tube 200, the connection channel 180, and the contaminated fluid outlet channel 120 are placed in a line with one another in the same plane, reduction in suction force generated by the external suction device can be minimized.

In conclusion, since the connection channel 180, the irrigation fluid inlet channel 130, and the contaminated fluid outlet channel 120 are placed in the same plane and the irrigation fluid control valve 300 and the drainage fluid control valve 400 are moved by external force to selectively open/close the irrigation fluid inlet channel 130 and the contaminated fluid outlet channel 120, supply of the irrigation fluid and suction of the contaminated fluid can be efficiently achieved with a simple structure.

Further, since the connection channel 180, the irrigation fluid inlet channel 130, and the contaminated fluid outlet channel 120 are shortened in length while being disposed in the same plane, the structure of the surgical instrument can be simplified, thereby allowing reduction in number of required components and thus reduction in manufacturing costs.

FIG. 3 is a view of the irrigation fluid control valve of the surgical instrument according to the present invention.

Referring to FIG. 1 to FIG. 3, the irrigation fluid control valve 300 is coupled to the instrument body 100 and is configured to be moved by external force and to be returned to an original position by elastic restoring force of the first elastic member 500.

The irrigation fluid control valve 300 may include a first valve head 310 exposed outside the main body 110, a first extension 320 downwardly extending from the first valve head 310, a first locking portion 330 downwardly extending from the first extension 320 and having a larger diameter than the first extension 320, and a first leg downwardly extending from the first locking portion 330.

The first leg includes a first upper leg 340 downwardly extending from the first locking portion 330, a first lower leg 350 downwardly extending from the first upper leg 340 and having a smaller cross-sectional width than the first upper leg 340, and a first terminal leg 360 downwardly extending from the first lower leg 350 and having a larger cross-sectional width than the first lower leg 350.

The first lower leg 350 is formed with a first communication hole 351 selectively communicating with the irrigation fluid inlet channel 130 and the contaminated fluid outlet channel 120.

In addition, the irrigation fluid control valve 300 further includes a first sealing portion 370 disposed on at least a portion of an outer surface of the first lower leg 350 to seal off the first installation space 140 from the irrigation fluid inlet channel 130 and the contaminated fluid outlet channel 120.

The first sealing portion 370 is formed therein with a first through-portion 373 to be fitted over the outer surface of the first lower leg 350. Here, the first sealing portion 370 is formed with a first sealing hole 371 communicating with the first communication hole 351.

However, it should be understood that the present invention is not limited thereto and the first sealing portion may be provided in the form of a coating layer on at least a portion of the first lower leg 350. For example, the first sealing portion may be formed by coating silicone or the like only on front and back surfaces of the first lower leg 350 in FIG. 3.

The first sealing portion 370 seals off the first installation space 140 from the irrigation fluid inlet channel 130 and the contaminated fluid outlet channel 120 while allowing the first sealing hole 371 to communicate with the first communication hole 351.

With the first sealing hole 371 aligned in position with the first communication hole 351, an inner surface of the first installation space 140 needs to closely contact an outer surface of the first sealing portion 370. To this end, the first sealing portion 370 may be formed of a material having good adhesion, such as silicone.

In addition, the irrigation fluid control valve 300 needs to be moved in the first installation space 140 by external force. To this end, a side surface 340a of the first upper leg, a side surface 370a of the first sealing portion, and a side surface 360a of the first terminal leg may be rounded such that the irrigation fluid control valve 300 can be smoothly moved in the first installation space 140.

If the side surface 340a of the first upper leg, the side surface 370a of the first sealing portion, and the side surface 360a of the first terminal leg are not rounded, a vacuum can be created in a lower region of the lower installation space 143 located at a lower end of the irrigation fluid control valve 300, making it difficult for the irrigation fluid control valve 300 to be moved freely.

However, it should be understood that the present invention is not limited thereto and the side surface of the first sealing portion may be beveled.

Since the first terminal leg 360 has a larger cross-sectional width than the first lower leg 350, the first sealing portion 370 disposed on the outer surface of the first lower leg 350 can be prevented from being separated from the first leg.

FIG. 4 is a view of the drainage fluid control valve of the surgical instrument according to the present invention.

Referring to FIG. 1, FIG. 2 and FIG. 4, the drainage fluid control valve 400 is coupled to the instrument body 100 and is separated a predetermined distance from the irrigation fluid control valve 300 in the longitudinal direction of the instrument body 100.

The drainage fluid control valve 400 includes a second valve head 410, a second extension 420, a second locking portion 430, a second leg, and a second sealing portion 470.

The second leg includes a second upper leg 440 downwardly extending from the second locking portion, a second lower leg 440 downwardly extending from the second upper leg 440 and having a smaller cross-sectional width than the second upper leg 440, and a second terminal leg 460 downwardly extending from the second lower leg 450 and having a larger cross-sectional width than the second lower leg 450.

Since the second valve head 410, the second extension 420, the second locking portion 430, the second upper leg 440, and the second terminal leg 460 are substantially the same as the first valve head 310, the first extension 320, the first upper leg 340, and the first terminal leg 360 of the irrigation fluid control valve, respectively, detailed description thereof will be omitted.

Unlike the first lower leg 350 of the irrigation fluid control valve, the second lower leg 450 is formed with a second communication hole 451 selectively communicating with the contaminated fluid outlet channel 120 and a third communication hole 453 selectively communicating with the irrigation fluid inlet channel 130.

In addition, the second sealing portion 470 is formed therein with a second through-portion 475 to be fitted over the outer surface of the second lower leg 450. Here, the second sealing portion 470 is formed with a second sealing hole 471 communicating with the second communication hole 451 and a third sealing hole 473 communicating with the third communication hole 453.

As in the irrigation fluid control valve, in the drainage fluid control valve 400, a side surface 440a of the second upper leg, a side surface 470a of the second sealing portion, and a side surface 460a of the second terminal leg may be rounded such that the drainage fluid control valve 400 can be smoothly moved in the second installation space 150.

However, it should be understood that the present invention is not limited thereto and the side surface of the second sealing portion may be beveled.

FIG. 5 is a view of the irrigation fluid control valve and the drainage fluid control valve of the surgical instrument according to the present invention with no external force applied thereto.

Referring to FIG. 2 and FIG. 5, the first elastic member 500 is disposed in the main body 110 to provide elastic restoring force against movement of the irrigation fluid control valve 300, and the second elastic member 600 is disposed in the main body 110 to provide elastic restoring force against movement of the drainage fluid control valve 400.

Specifically, the first elastic member 500 is supported at one side thereof on a bottom of the first upper installation space 141 and is supported at the other side thereof on a lower surface of the first locking portion 330 to provide elastic restoring force acting in the opposite direction of external force applied to the irrigation fluid control valve 300.

Since the installation position and function of the second elastic member 600 are substantially the same as those of the first elastic member 500, detailed description thereof will be omitted.

As shown in FIG. 5, when no external force is applied, the irrigation fluid control valve 300 opens the contaminated fluid outlet channel 120 while closing the irrigation fluid inlet channel 130 and the drainage fluid control valve 400 closes the contaminated fluid outlet channel 120 while opening the irrigation fluid inlet channel 130.

In other words, when no external force (that is, pressing force) is applied to the irrigation fluid control valve 300 and the drainage fluid control valve 400, the irrigation fluid inlet channel 130 and the contaminated fluid outlet channel 120 are both closed.

FIG. 6 is a view of the irrigation fluid control valve and the drainage fluid control valve of the surgical instrument according to the present invention with external force applied only to the irrigation fluid control valve, FIG. 7 is a view of the irrigation fluid control valve and the drainage fluid control valve of the surgical instrument according to the present invention with external force applied only to the drainage fluid control valve, and FIG. 8 is a view of the irrigation fluid control valve and the drainage fluid control valve of the surgical instrument according to the present invention with external force applied to both the irrigation fluid control valve and the drainage fluid control valve.

As shown in FIG. 6, when the irrigation fluid control valve 300 is moved in a first direction, that is, in a direction of an inner space of the main body 110, by external force with no external force applied to the drainage fluid control valve 400, the irrigation fluid control valve 300 closes the contaminated fluid outlet channel 120 while opening the irrigation fluid inlet channel 130 such that the irrigation fluid can be supplied into the body of the patient along the irrigation fluid inlet channel 130.

Here, since the drainage fluid control valve 400 remains in a position closing the contaminated fluid outlet channel 120 and opening the irrigation fluid inlet channel 130, ultimately, only the irrigation fluid inlet channel 130 is open.

When external force applied to the irrigation fluid control valve 300, that is, pressing force of a user, is removed, the irrigation fluid control valve 300 is moved in an opposite direction with respect to the first direction by elastic restoring force of the first elastic member 500.

Here, the first locking portion 330 of the irrigation fluid control valve 300 is caught by a bent portion 161 of the first retention cap, thereby preventing the irrigation fluid control valve 300 from being separated from the main body 110.

That is, when external force applied to the irrigation fluid control valve 300 is removed, the surgical instrument is returned to the state shown in FIG. 5.

As shown in FIG. 7, when the drainage fluid control valve 400 is moved in the first direction, that is, in the direction of the inner space of the main body 110, by external force with no external force applied to the irrigation fluid control valve 300, the drainage fluid control valve 400 closes the irrigation fluid inlet channel 130 while opening the contaminated fluid outlet channel 120 such that the contaminated fluid can be suctioned out of the body of the patient along the contaminated fluid outlet channel 120.

Here, since the irrigation fluid control valve 300 remains in a position opening the contaminated fluid outlet channel 120 and closing the irrigation fluid inlet channel 130, ultimately, only the contaminated fluid outlet channel 120 is open.

When external force applied to the drainage fluid control valve 400, that is, pressing force of a user, is removed, the drainage fluid control valve 400 is moved in an opposite direction with respect to the first direction by elastic restoring force of the second elastic member 600.

Here, the second locking portion 430 of the drainage fluid control valve 400 is caught by a bent portion 171 of the second retention cap, thereby preventing the drainage fluid control valve 400 from being separated from the main body 110.

As shown in FIG. 8, when a user inadvertently presses both the irrigation fluid control valve 300 and the drainage fluid control valve 400, the irrigation fluid control valve 300 opens the irrigation fluid inlet channel while closing the contaminated fluid outlet channel 120.

At the same time, the drainage fluid control valve 400 closes the irrigation fluid inlet channel 130 while opening the contaminated fluid outlet channel.

In conclusion, when external force is applied to both the irrigation fluid control valve 300 and the drainage fluid control valve 400, the irrigation fluid inlet channel 130 and the contaminated fluid outlet channel 120 are both closed.

FIG. 9 is a view of a surgical instrument for suction and irrigation according to another embodiment of the present invention.

The surgical instrument of FIG. 9 has a similar structure to the surgical instrument according to the above embodiment. The same components as in the surgical instrument according to the above embodiment will be denoted by the same reference numerals as in the surgical instrument according to the above embodiment, and detailed description thereof will be omitted.

However, unlike in the surgical instrument according to the above embodiment, the instrument body 100 according to this embodiment further includes a first elastic member installation portion 191 for installation of the first elastic member 500 and a second elastic member installation portion 192 for installation of the second elastic member 600.

The first elastic member installation portion 191 protrudes a predetermined height from the bottom of the first upper installation space 141. The first elastic member 500 is disposed around the first elastic member installation portion 191 and the irrigation fluid control valve 300 is inserted into the instrument body 100 while passing through the first elastic member installation portion 191.

Similarly, the second elastic member installation portion 192 protrudes a predetermined height from the bottom of the second upper installation space 151. The second elastic member 600 is disposed around the second elastic member installation portion 192 and the drainage fluid control valve 400 is inserted into the instrument body 100 while passing through the second elastic member installation portion 192.

As a result, the first elastic member 500 and the second elastic member 600 are further inserted into the instrument body 100 by the heights of the first elastic member installation portion 191 and the second elastic member installation portion 192, respectively.

Accordingly, the heights of the first retention cap 163 and the second retention cap 173 coupled to the upper portion of the instrument body 100 can be reduced to reduce the overall height of the surgical instrument, whereby a user can conveniently operate the surgical instrument.

Although some embodiments have been described herein, it should be understood by those skilled in the art that these embodiments are given by way of illustration only and the present invention is not limited thereto. In addition, it should be understood that various modifications, variations, and alterations can be made by those skilled in the art without departing from the spirit and scope of the present invention. Therefore, the scope of the invention should be limited only by the accompanying claims and equivalents thereto.

INDUSTRIAL APPLICABILITY

In laparoscopic surgery, a surgical instrument which supplies an irrigation fluid for irrigation of a surgical site of a patient and discharges a contaminated fluid from the body of the patient after irrigation of the surgical site of the patient, that is, a laparoscopic suction and irrigation system, is used.

In the surgical instrument for suction and irrigation according to the present invention, which corresponds to such a laparoscopic suction and irrigation system, the irrigation fluid inlet channel, the contaminated fluid outlet channel, the irrigation fluid control valve, and the drainage fluid control valve are placed in the same plane in the longitudinal direction of the instrument body and the irrigation fluid inlet channel and the drainage fluid control valve are moved by external force to selectively open/close the irrigation fluid inlet channel and the contaminated fluid outlet channel. Thus, the surgical instrument for suction and irrigation according to the present invention can achieve efficient supply of an irrigation fluid and efficient suction of a contaminated fluid with a simple structure and thus can be widely used in related industries.

The invention claimed is:

1. A surgical instrument for suction and irrigation, comprising:
    an insertion tube configured to be inserted into the body of a patient;
    an instrument body coupled to the insertion tube and configured to be disposed outside the body of the patient;
    an irrigation fluid control valve coupled to the instrument body; and
    a drainage fluid control valve coupled to the instrument body and separated a predetermined distance from the irrigation fluid control valve in a longitudinal direction of the instrument body,
    wherein the instrument body comprises a main body, the main body being formed with a connection channel communicating with the insertion tube, an irrigation fluid inlet channel branched off of the connection channel and adapted to supply an irrigation fluid into the body of the patient therethrough, and a contaminated fluid outlet channel branched off of the connection channel and adapted to suction a contaminated fluid therethrough after irrigation of an inside of the body of the patient, and
    each of the irrigation fluid control valve and the drainage fluid control valve is disposed in the instrument body to pass through both the irrigation fluid inlet channel and the contaminated fluid outlet channel and is moved by external force to selectively open/close the irrigation fluid inlet channel and the contaminated fluid outlet channel,
    wherein the irrigation fluid control valve comprises:
    a first valve head exposed outside the main body;
    a first extension downwardly extending from the first valve head,
    a first locking portion downwardly extending from the first extension and having a larger diameter than the first extension; and
    a first leg downwardly extending from the first locking portion, and
    wherein the first leg comprises:
    a first upper leg downwardly extending from the first locking portion; and
    a first lower leg downwardly extending from the first upper leg and having a smaller cross-sectional width than the first upper leg, the first lower leg being formed with a first communication hole selectively communicating with the irrigation fluid inlet channel and the contaminated fluid outlet channel.

2. The surgical instrument according to claim 1, wherein, when no external force is applied, the irrigation fluid control valve opens the contaminated fluid outlet channel while closing the irrigation fluid inlet channel, and the drainage fluid control valve opens the irrigation fluid inlet channel while closing the contaminated fluid outlet channel.

3. The surgical instrument according to claim 2, wherein, when the irrigation fluid control valve is moved in a first direction corresponding to a direction of an inner space of the main body by external force with no external force applied to the drainage fluid control valve, the irrigation fluid control valve closes the contaminated fluid outlet channel while opening the irrigation fluid inlet channel such that the irrigation fluid is supplied into the body of the patient along the irrigation fluid inlet channel.

4. The surgical instrument according to claim 2, wherein, when the drainage fluid control valve is moved in a first direction corresponding to a direction of an inner space of the main body by external force with no external force applied to the irrigation fluid control valve, the drainage fluid control valve closes the irrigation fluid inlet channel while opening the contaminated fluid outlet channel such that the contaminated fluid is suctioned out of the body of the patient along the contaminated fluid outlet channel.

5. The surgical instrument according to claim 1, further comprising:
    a first elastic member disposed in the main body to provide elastic restoring force against movement of the irrigation fluid control valve; and
    a second elastic member disposed in the main body to provide elastic restoring force against movement of the drainage fluid control valve.

6. The surgical instrument according to claim 1, wherein the main body is formed with a first installation space into which the irrigation fluid control valve is partially inserted and a second installation space into which the drainage fluid control valve is partially inserted, the first installation space comprising a first upper installation space and a first lower installation space downwardly extending from the first upper installation space and having a smaller cross-sectional width than the first upper installation space.

7. The surgical instrument according to claim 6, wherein the instrument body further comprises a first retention cap coupled to the main body to prevent the irrigation fluid control valve from being separated from the main body, the first retention cap being coupled to an upper edge of the first upper installation space.

8. The surgical instrument according to claim 6, wherein the irrigation fluid control valve further comprises a first sealing portion disposed on at least a portion of an outer surface of the first lower leg to seal off the first installation space from the irrigation fluid inlet channel and the contaminated fluid outlet channel, the first sealing portion being formed with a first sealing hole communicating with the first communication hole.

9. The surgical instrument according to claim 8, wherein a side surface of the first upper leg and a side surface of the first sealing portion are rounded to allow the irrigation fluid control valve to be smoothly moved in the first installation space.

10. The surgical instrument according to claim 1, wherein the drainage fluid control valve is formed with a second communication hole selectively communicating with the contaminated fluid outlet channel and a third communication hole selectively communicating with the irrigation fluid inlet channel.

11. The surgical instrument according to claim 1, wherein a central cross-section of the connection channel, a central cross-section of the irrigation fluid inlet channel, and a central cross-section of the contaminated fluid outlet channel are placed in a same plane located in the longitudinal direction of the instrument body.

* * * * *